United States Patent [19]

Saito et al.

[11] Patent Number: 5,073,500
[45] Date of Patent: Dec. 17, 1991

[54] METHOD AND APPARATUS FOR DETECTING URINARY CONSTITUENTS

[75] Inventors: Shiro Saito; Kenji Shirai; Ryuichi Kawamoto; Shigeru Sakakibara, all of Aichi, Japan

[73] Assignee: Inax Corporation, Aichi, Japan

[21] Appl. No.: 291,168

[22] Filed: Dec. 28, 1988

[30] Foreign Application Priority Data

| Jan. 8, 1988 | [JP] | Japan | 63-2729 |
| Jan. 8, 1988 | [JP] | Japan | 63-2730 |
| Feb. 15, 1988 | [JP] | Japan | 63-32353 |
| Jun. 2, 1988 | [JP] | Japan | 63-73675[U] |
| Jul. 16, 1988 | [JP] | Japan | 63-177595 |
| Jul. 16, 1988 | [JP] | Japan | 63-177596 |

[51] Int. Cl.$^5$ ............................................. G01N 35/08
[52] U.S. Cl. ................................. 436/53; 436/174; 4/300; 4/340; 4/341; 128/760; 128/771; 422/82
[58] Field of Search ............ 422/82; 436/53, 174; 4/300, 340, 341; 128/760, 771

[56] References Cited

U.S. PATENT DOCUMENTS

| 4,253,846 | 3/1981 | Smythe et al. | 422/82 |
| 4,860,767 | 8/1989 | Maekawa | 128/760 |
| 4,865,811 | 9/1989 | Newton et al. | 422/82 |
| 4,943,416 | 7/1990 | Kikuchi et al. | 422/64 |

*Primary Examiner*—Peter Chin
*Attorney, Agent, or Firm*—Oliff & Berridge

[57] ABSTRACT

A method and an apparatus for measuring the concentration values of constituents of urine collected in a toilet bowl. A conduit extends from the urine-collecting portion of the bowl to a concentration-measuring device. A gas injector is mounted beside the conduit to intermittently inject gas into the conduit, for dividing the urine contained in the conduit into aliquots. The concentration values of urinary constituents of each aliquot are measured.

22 Claims, 15 Drawing Sheets

METHOD AND APPARATUS FOR DETECTING URINARY CONSTITUENTS

FIELD OF THE INVENTION AND RELATED ART STATEMENT

The present invention relates to a method and an apparatus for measuring the values of concentration of certain urinary constituents and, more particularly, to a method and an apparatus capable of investigating numerous components of urine successively in a short time. The invention also relates to an apparatus capable of detecting or analyzing urinary constituents after a toilet bowl is used. More specifically, it relates to an apparatus which preserves data on each individual user of the bowl and treats the data to monitor the health of each individual user for a long term.

An apparatus including a device mounted in a toilet bowl for detecting, investigating, or analyzing urinary constituents immediately after the bowl is used has been proposed. The device mounted in the bowl is a detector for detecting certain components of urine, a measuring instrument for measuring the concentration values of the components, or an analytical instrument for analyzing the components.

This known apparatus consists essentially of a urine-collecting portion mounted in a toilet bowl, an analytical instrument, and an indicator. Urine is collected by the urine-collecting portion and fed into the analytical instrument where urinary components are analyzed. The results of the analysis are displayed. Another known apparatus includes a urinary component detector mounted on the lower portion of a toilet bowl. Simultaneously with the use of the bowl, certain components of urine are detected, and the results are displayed.

A conventional toilet bowl equipped with an instrument for measuring the concentration values of certain components of urine is disclosed in Japanese Patent Laid-Open No. 217,844/1984. This bowl is shown in FIG. 4, where it is indicated by numeral 20 and has a urine-collecting portion 21. The urine collected by the collecting portion 21 is sent via a filter 28 to a liquid chromatograph 24 by a pump 22. The urine is forced through the chromatograph 24 to separate a certain component of the urine. The absorbance of the separated urinary component is measured by photometers 25 and 26 to determine the concentration. The results are indicated by an indicator 27.

Generally, the time taken for a substance to pass through a liquid chromatograph is intrinsic in the substance and determined by the molecular weight, the size of the molecule, and other factors. On this principle, urine is introduced into a liquid chromatograph. After a lapse of a certain time, the absorbance of the effluent from the chromatograph with respect to a given wavelength is measured. In this way, the concentration of a certain constituent can be determined. In the technique disclosed in the above-cited Japanese Patent Laid-Open No. 217,844/1984, after a lapse of 13 seconds since the introduction of urine into a liquid chromatograph, the absorbance of the effluent is measured with a wavelength of 254 nm or 306 nm to determine the concentration of the sugar or glucose.

The aforementioned urinary component-investigating instrument for use with a toilet bowl employs a liquid chromatograph to separate certain components of urine. Since this liquid chromatograph is a very sophisticated instrument, it is expensive and difficult to handle. Furthermore, once it is used to measure the absorbance of a urinary constituent, it must be cleaned carefully in a sufficient time to make preparations for the next measurement. Therefore, a quite long time is needed for each measurement. This deteriorates the efficiency and makes it difficult to put the instrument into practical use.

After a urinary component is detected, investigated, or analyzed by the above-described conventional apparatus, the results are only indiated in the form of numerical values. For this reason, it is difficult to understand how the health of each individual person has changed. Especially, when the result is represented in terms of a single numerical value, it is almost impossible for one which has no expertise to see whether the examinee has been maintained in good health. A patient's primary concern is to know whether he or she is getting better or worse, but the patient cannot immediately get the requisite knowledge from the results of the measurement. In this way, the conventional apparatus cannot fulfill the object it was intended, i.e., health surveillance. Thus, it conspicuously lacks practicability.

OBJECTS AND SUMMARY OF THE INVENTION

In view of the foregoing problems, the present invention has been made.

It is an object of the invention to provide a method and a toilet bowl capable of measuring the concentration of each of numerous urinary constituents successively in a short time.

It is another object of the invention to provide an apparatus which compares the results of a measurement or analysis presently made of urine with data obtained previously or otherwise treats data and displays the result of the comparison to permit one to monitor a person's health for a long period.

In one feature of a method of measuring the concentration of urinary constituents by collecting urine from a toilet bowl in accordance with the invention, a gas injector is disposed in a conduit which carries urine from the urine-collecting portion to a concentration-measuring device to intermittently inject gas into the conduit, for dividing the urine contained in the conduit into numerous aliquots. The concentration of each aliquot is measured.

A toilet bowl for carrying out the measuring method described in the preceding paragraph in accordance with the invention has a urine-collecting portion with which a conduit is connected to send the urine collected by the collecting portion to a concentration-measuring device, for measuring the concentration of each urinary component. This bowl is characterized in that a gas injector for intermittently injecting gas into the conduit is disposed beside the conduit.

In accordance with the invention, when the urine collected by the urine-collecting portion of the toilet bowl is being forced into the concentration-measuring device, the gas injector disposed beside the conduit injects gas into the urine intermittently. This divides the urine in the conduit into plural aliquots. The aliquots are fed to the concentration-measuring device one after another and their concentration values are successively measured. Thus, numerous constituents of urine can be investigated successively in a short time.

The above objects are achieved in accordance with the teachings of the invention by the provision of an optically measuring toilet bowl comprising a urine-collecting portion, light-emitting devices for projecting light into the urine collected by the collecting portion, and a light-receiving portion that receives the light transmitted through the urine. The concentration of a certain urinary component is determined from its absorbance. This bowl is characterized in that the light-emitting devices emit different wavelengths of light. The two light rays emitted from the light-emitting devices are superimposed, resulting in light of another wavelength. The produced light that is closer to the wavelength at which a certain urinary component shows a maximum absorbance is projected into the urine. Consequently, the absorbance of the urinary component can be measured more accurately. Hence, the concentration can be determined with higher accuracy.

In one aspect of the invention, a reagent is intermittently injected by a reagent injector into each aliquot of urine. The reagent is added to each aliquot so as to form plural droplets. As a result, the reagent and the aliquot are mixed well. Then, the aliquots are sent to a concentration-measuring device one after another to measure their values of concentration successively. Hence, a number of urinary constituents can be investigated successively in a short time with quite high accuracy.

In another aspect of the invention, the urine collected by the urine collecting portion of a toilet bowl is channeled through a conduit connected with the collecting portion. A reagent is added to the urine. The resulting sample is caused to pass through a light-transmitting portion formed in the conduit. The light-transmitting portion comprises a light-emitting diode or other light source which projects light into the urine moving through the light-transmitting portion. The light transmitted through the sample is received by a photodiode or other light-receiving device. The concentration of a urinary component is determined from the amount of received light. A condenser lens is mounted between the light source and the sample. The light gathered by the lens is caused to hit the sample. In this way, the light emanating from the light source is once gathered by the condenser lens and then directed into the sample. Therefore, the sample is efficiently illuminated with the light coming from the light source. This increases the amount of light falling on the light-receiving device, thus enhancing the accuracy with which the concentration of a urinary component is measured.

In a further aspect of the invention, a urine collector having a diluting means is mounted in a toilet bowl to force diluted urine through a conduit. It is not necessary to mount a diluting means in the conduit and so the conduit can be made short. Also, the whole apparatus can be rendered small.

In a still other aspect of the invention, a toilet bowl has a urine-collecting portion connected with a conduit. The urine collected by the collecting portion is fed to a component analyzer through the conduit to analyze urinary components. Output data from the analyzer is stored in a processing unit, which can read and process the data. Further, a display means is provided to display the results of the processing of the data.

In a yet other aspect of the invention, a health surveillance apparatus has a urine component detector mounted in a toilet bowl. Also, a processing unit is provided to store the output data from the detector. The processing unit can process data in a predetermined manner. The output data from the processing unit is displayed on a display means. In the health surveillance apparatus, a signal indicating the results of analysis or detection of a urinary component is fed to the processing unit. Then, data is processed appropriately. For example, data derived presently is compared with data obtained previously. The results of the processing are displayed. This enables one to quickly understand the changes in his or her health with time. Since the results of processing of data based on data presently obtained from urine and on data previously obtained are displayed, even a layman can easily see whether he or she is in good health or not. Also, data about each individual person is preserved and, therefore, changes in health can be quickly grasped. Thus, the inventive apparatus greatly contributes to health surveillance and yields great practical advantages.

DETAILED DESCRIPTION OF THE PREFERRED EMBODIMENTS

Figure 1:
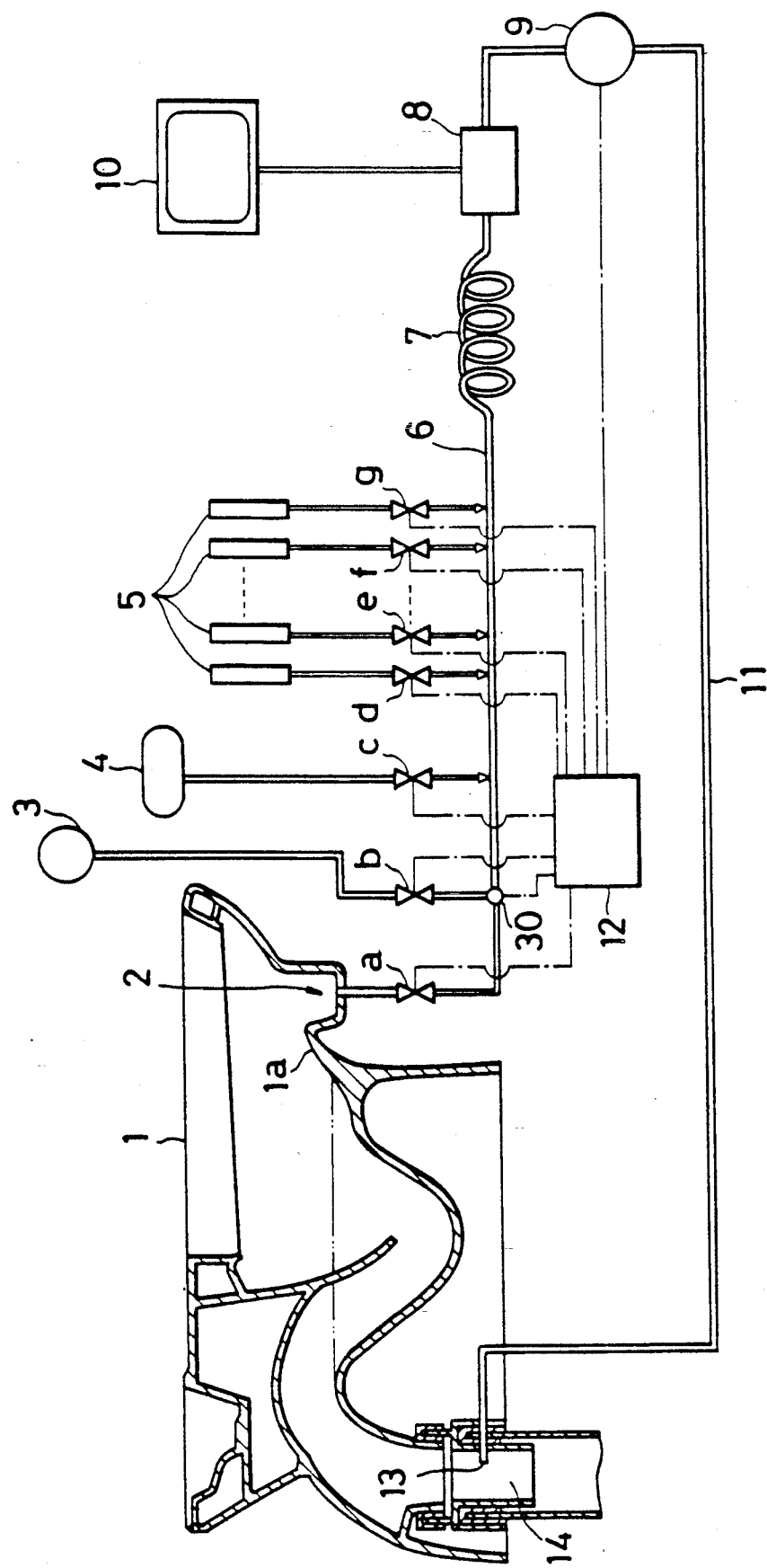
FIG. 1 is a schematic representation of a urine constituent-investigating apparatus according to the invention.

An apparatus for investigating urinary components in accordance with the invention is schematically shown in FIG. 1. The apparatus comprises a toilet bowl the body of which is indicated by numeral 1. A urine-collecting portion 2 is formed at a suitable location on the lower portion 1a of the body 1 of the bowl. A conduit 6 for directing urine to a concentration-measuring device 8 is connected to the bottom of the urine-collecting portion 2. The measuring device 8 measures the concentration values of urinary constituents. A diluting means 3 for diluting the collected urine by an appropriate factor, a gas injector 4 for intermittently injecting gas into the urine contained in the conduit 6, reagent adders 5 for adding reagents to the urine, and a mixing means 7 for homogeneously mixing together the urine and the reagents are connected to the conduit 6. A pump 9 is disposed downstream of the concentration-measuring device 8 to control the flow of urine in the conduit 6. A return pipe 11 is connected to the pump 9. The body 1 of the bowl has a discharge portion 14 into which the rear end 13 of the return pipe 11 is connected.

Using the apparatus constructed as described above, the concentration values of urinary constituents are measured in the manner described below. Urine is collected by the urine-collecting portion 2. Of the collected urine, a certain amount is supplied into the conduit 6 via a valve a. If necessary, the urine is diluted by the diluting means 3. For this purpose, diluting liquid, such as distilled water, supplied from the diluting means 3 and the collected urine are mixed at a given ratio, using a mixing valve 30.

Figure 3:
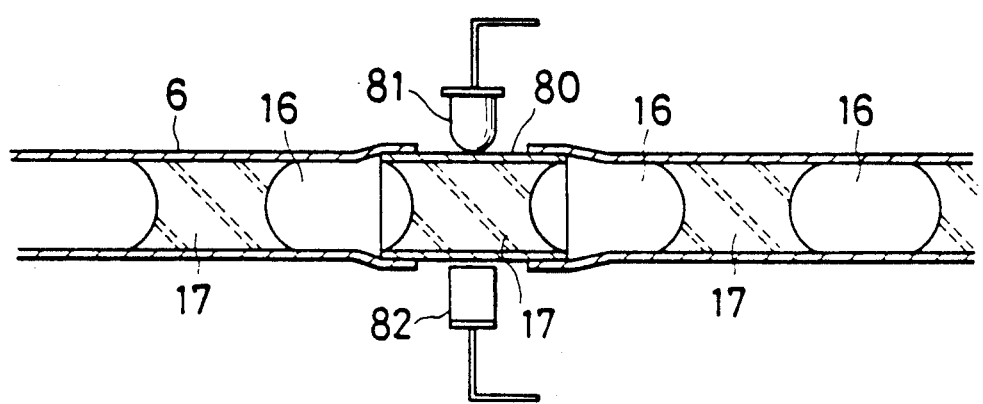
FIG. 3 is an enlarged cross section of a concentration-measuring device.
Figure 4:
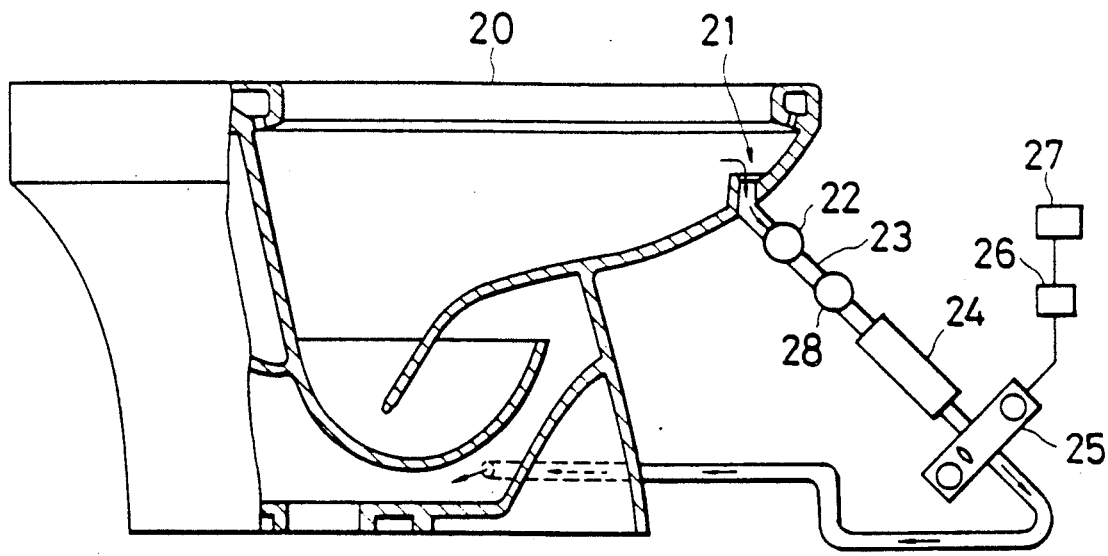
FIG. 4 is a partially cutaway side elevation of a conventional urine constituent-investigating toilet bowl.

Then the gas injector 4 intermittently injects gas into the urine contained in the conduit 6 to divide the urine 15 into a plurality of aliquots 17 which are separated by air bubbles 16. The injected gas can be air. Instead, an inert gas such as nitrogen can be used. After the urine is divided into the aliquots 17, appropriate reagents are added to the aliquots 17. When the concentration values of numerous constituents are measured, the same number of reagent adders 5 as the urinary constituents to be investigated are preferably prepared. After reagents are added to the aliquots, the urine is mixed with the reagents uniformly by the mixing means 7. In the illustrated example, the conduit 6 is shaped into a spiral form to promote mixing of the urine and the reagents by forcing them through the spiral conduit. Then the aliquots 17 of the urine are successively fed to the concentration-measuring device 8. This permits the concentration values of different urinary constituents to be successively measured. Therefore, the urine can be examined for many items in a short time. A display device 10 is connected to the concentration-measuring device 8 to quickly indicate the results of measurement.

Where the absorbance of urine is measured to determine the concentration of a urinary component, a spectrophotometer is used as the concentration-measuring device 8. As shown in FIG. 3, a part of the conduit 6 can be replaced with a glass tube 80, and a light-emitting diode 81 and a light-receiving photodiode 82 can be disposed on opposite sides of the glass tube 80 to measure the absorbance with respect to a certain wavelength of light. Where ultraviolet rays are projected into the urine to measure the concentration of protein or glucose, it is desired to fabricate the glass tube 80 from quartz glass or other similar material.

After the measurement of the concentration values of constituents are finished, the urine is returned to the body 1 of the bowl through the return pipe 11 and then discharged into the discharge portion 14. After the end of the measurement, flushing water which is supplied either from the body 1 of the bowl or from a cleaning nozzle (not shown) disposed on the urine-collecting portion 2 is forced through the conduit 6 by the pump 9 to clean the inside of the conduit 6.

A controller 12 can be disposed to automate the above-described measurement of the concentration values of the urinary components. Specifically, the valve a for controlling the amount of urine introduced into the conduit 6, another valve b for controlling the amount of the diluting liquid supplied from the diluting means 3, the mixing valve 30 for controlling the rate of dilution, a gas valve c for intermittently injecting the gas supplied from the gas injector 4, reagent valves d-g for controlling the addition of reagents to the aliquots, and the pump 9 for controlling the flow of urine inside the conduit 6 are connected with the controller 12. The steps necessary to measure the concentration values of urinary constituents are controlled by the controller 12.

It is to be understood that the present invention is not limited to the above example and that various changes and modifications are possible. For example, the urine may be diluted in the urine-collecting portion before it is admitted into the conduit, or the aliquots of urine divided by intermittent injection of gas may be diluted successively. In the latter case, the rate of dilution can be changed for every aliquot. The dilution step may be omitted by adding sufficient amounts of reagents, e.g. two or more times as much as each aliquot, to each aliquot after the urine is divided into aliquots. The reagents added to the aliquots can be different in kind. Also, the reagents can be alike in kind but differ in concentration. This is useful where the concentration of the urinary component under investigation is unknown. The concentration of a component can be determined by measuring the pH with a pH meter, as well as by measuring the absorbance with a spectrophotometer. Measurements may also be made with an enzyme sensor or BOD (biochemical oxygen demand) sensor.

As shown in FIG. 3, a part of the conduit 6 is replaced with the glass tube 80. The light-emitting diode 81 and the light-receiving photodiode 82 are disposed on opposite sides of the glass tube 80. The absorbance with respect to a certain wavelength of light is measured. This arrangement yields the following advantage. Generally, each different substance shows its maximum absorbance at a different wavelength. Also, the wavelength of light that is easily absorbed varies according to the kind of urinary constituent. A spectrophotometer (not shown) is connected with the photodiode 82 to measure the absorbance at a given wavelength of light. Thus, the concentration of a desired urinary constituent can be determined. A reagent causes a color reaction with a certain urinary component. This makes it easy to measure the absorbance and to determine the concentration of a urinary constituent.

As an example, protein contained in urine exhibits its maximum absorbance at a wavelength of 600 nm. If the LED 81 emits orange light having a peak wavelength of 610 nm close to the above-described 600 nm, then the light emitted from the LED 81 is absorbed by the protein contained in the urine. The transmitted light falls on the light-receiving photodiode 82. Then, the concentration of the protein in the urine can be determined from the formula stating the relationship of the output from the photodiode 82 to the concentration of the protein.

The wavelength at which glucose contained in urine shows its maximum absorbance is 505 nm. Using an LED emitting green light whose peak wavelength is 565 nm, the concentration of the glucose contained in the urine can be known from the absorbance.

The wavelength at which urobilinogen shows its maximum absorbance is 562 nm. An LED producing green light having a peak wavelength of 565 nm can be employed to measure the concentration of the urobilinogen.

The wavelength at which occult blood in urine exhibits its maximum absorbance is estimated to be between 550 and 560 nm and so the use of an LED emitting orange light having a peak wavelength of 610 nm is preferred in measuring the concentration of the occult blood.

Figure 15:
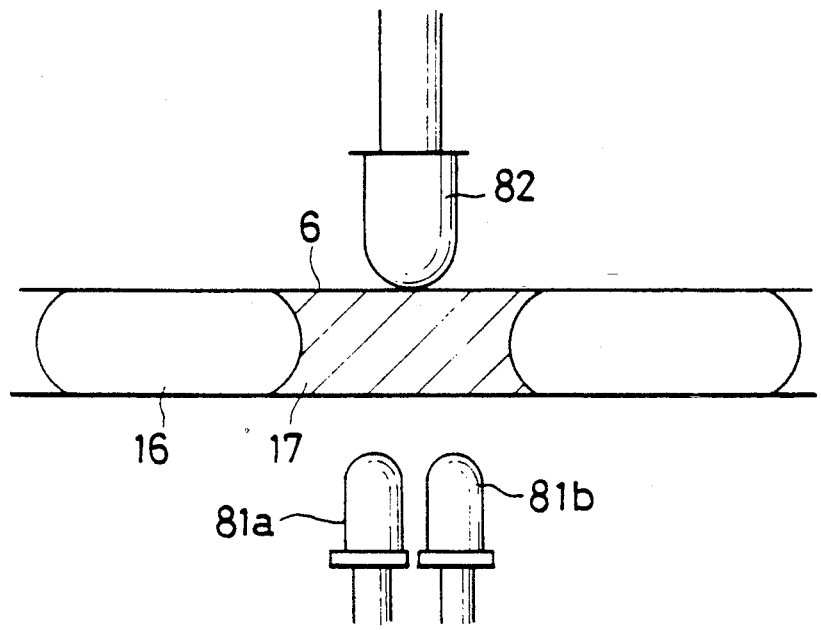
FIG. 15 is a schematic representation of a concentration-measuring device.
Figure 16:
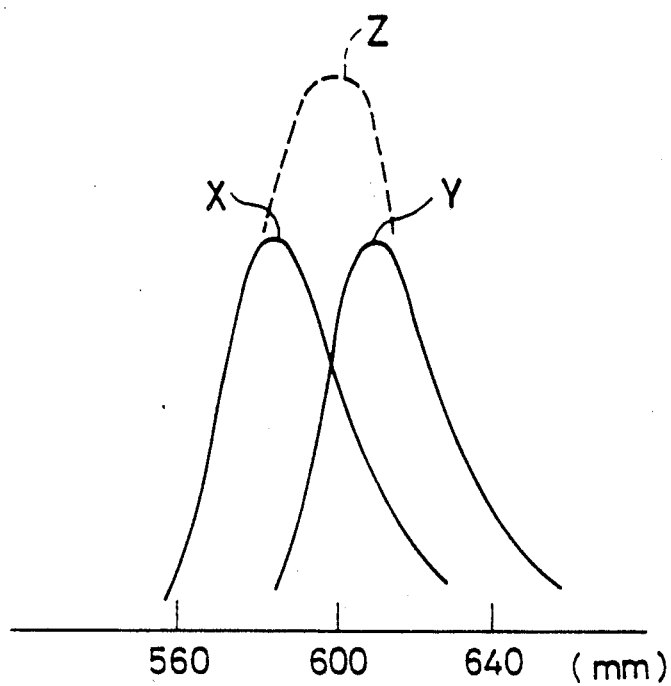
FIG. 16 is a graph showing the wavelength characteristic of light falling on the photodiode of the measuring device shown in FIG. 15.

In order to measure the concentration of a certain substance present in urine with higher accuracy, it is necessary to project light having a peak wavelength closer to the wavelength at which the substance shows its maximum absorbance and to measure the absorbance at the wavelength of the projected light. As shown in FIG. 15, two LEDs 81a and 81b emitting light rays having different peak wavelengths are juxtaposed. A photodiode 82 is disposed opposite to the LEDs. Referring also to FIG. 16, the LED 81a produces yellow light having a peak wavelength of 585 nm. The characteristic of the yellow light is indicated by X in FIG. 16. The LED 81b emits orange light having a peak wavelength of 610 nm. The characteristic of the orange light is indicated by Y. When the two LEDs emit the two kinds of light of different wavelengths simultaneously, light having a peak wavelength of about 600 nm as indicated by Z can be obtained. This wavelength is closest to the wavelength 600 nm at which protein shows its maximum absorbance and, therefore, the concentration of the protein contained in urine can be measured with higher accuracy.

In this way, where two or more LEDs having different peak wavelengths are utilized, the wavelength at which the urinary constituent to be investigated shows its maximum absorbance can be approximated at all times. Hence, the measurement can be made more accurately.

Figure 5:
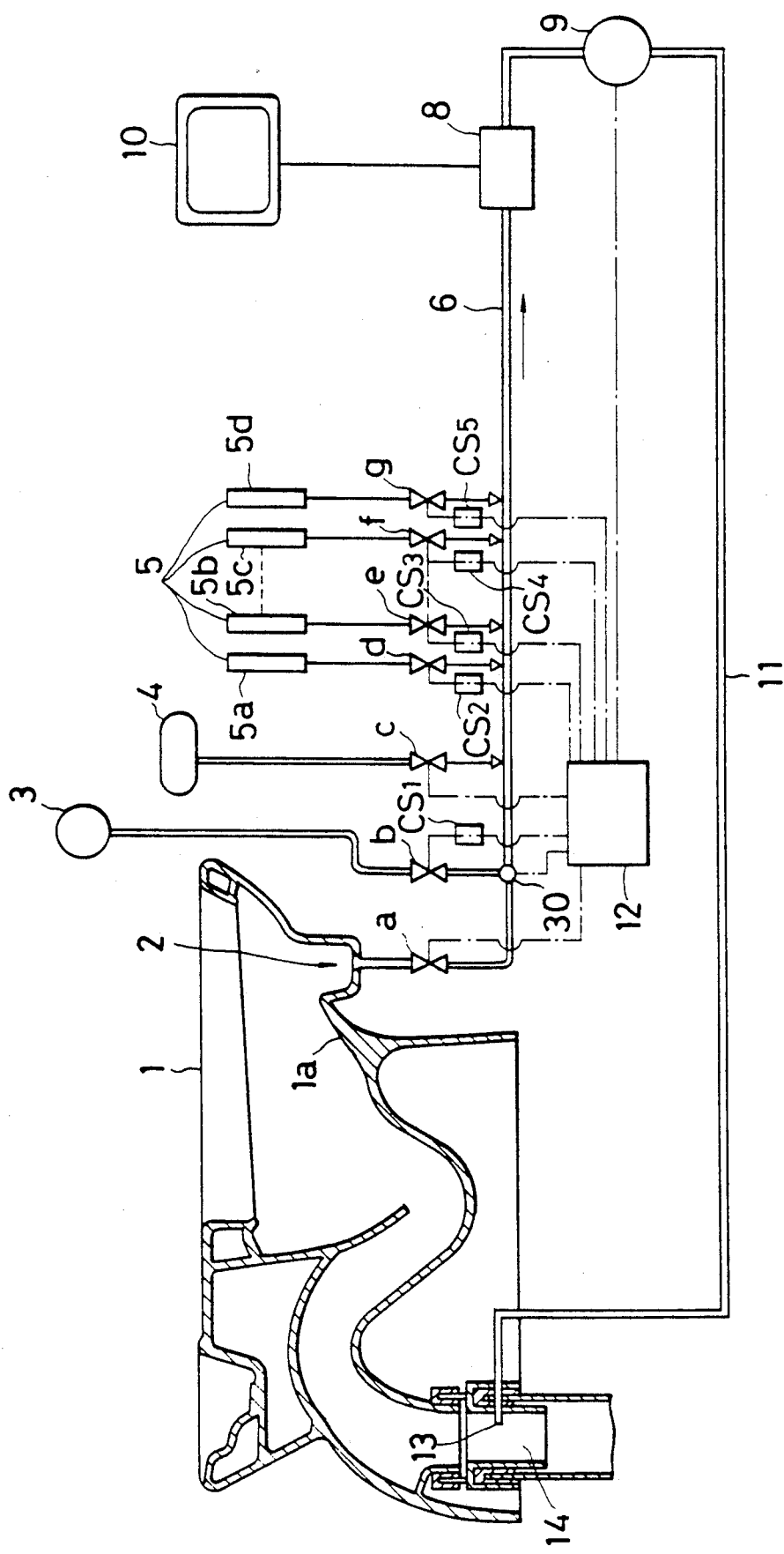
FIG. 5 is a diagram of another urine constituent-investigating toilet bowl according to the invention.

FIG. 5 schematically shows another measuring apparatus according to the invention. It is to be noted that like components are denoted by like reference numerals in both FIGS. 1 and 5. This apparatus has a solenoid valve a which is controlled by a main controller 12. The diluting means 3, the gas injector 4, and the reagent adders 5 are equipped with a solenoid valve b, a solenoid valve c, and solenoid valves d, e, f, g, respectively. The main controller 12 can also control these valves b–g. Sub controllers $cs_1$–$cs_5$ are connected with the solenoid valves b, d, e, f, g, respectively, and with the main controller 12.

When urine flowing down the conduit 6 arrives at a certain position, the main controller 12 senses the arrival and signals the solenoid valve b that controls injection of diluting liquid supplied from the diluting means 3. The valve b intermittently opens or closes under the control of the sub controller $cs_1$. For instance, the valve injects the liquid into the conduit 6 two to four times.

Figure 2:
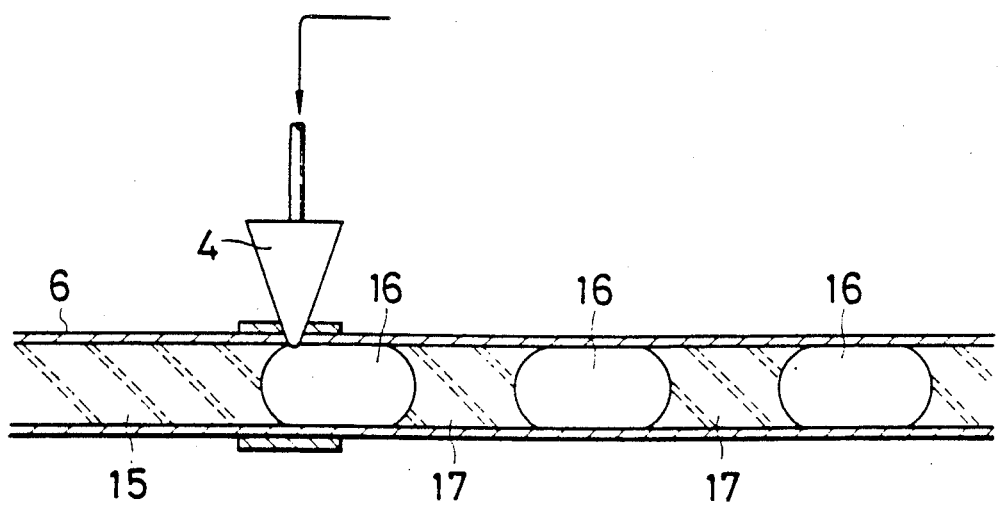
FIG. 2 is an enlarged cross section of aliquots of urine.

The gas injector 4 injects gas into the conduit 6 via the solenoid valve c that is controlled by the main controller 12. The gas is injected into urine intermittently. As shown in FIG. 2, the urine 15 contained in the conduit 6 is divided into plural aliquots 17 which are separated by the injected gas bubbles 16. For example, the aliquots 17 can be spaced a distance of 20 mm from each other. Subsequently, suitable reagents are added to the aliquots 17.

When the concentration values of numerous urinary components are measured, the same number of reagent adders 5 as the urinary components to be investigated are prepared. In the present example, the reagent adders 5 are four in number. As shown in FIG. 5, a reagent adder 5a is disposed to add a reagent for detecting glucose present in urine. A reagent adder 5b used for detection of protein in urine is disposed to the right of the adder 5a. A reagent adder 5c used for detection of urobilinogen existing in urine is mounted to the right of the adder 5c. A reagent adder 5d used for detection of occult blood in urine is located to the right of the adder 5c.

The reagent adder 5a can contain a reagent used for detection of glucose, such as glucose oxidase or copper sulfate. The reagent adder 5b can contain a reagent used for detection of protein, such as pyrogallol red-molybdic acid, sulfosalicylic acid, or trichloroacetic acid. The reagent adder 5c can contain a reagent used for detection of urobilinogen, such as an aldehyde reagent or Ehrlich's reagent. The reagent adder 5 can hold a reagent used for detection of occult blood present in urine, such as phenolphthalein or orthotolidine.

Figure 6:
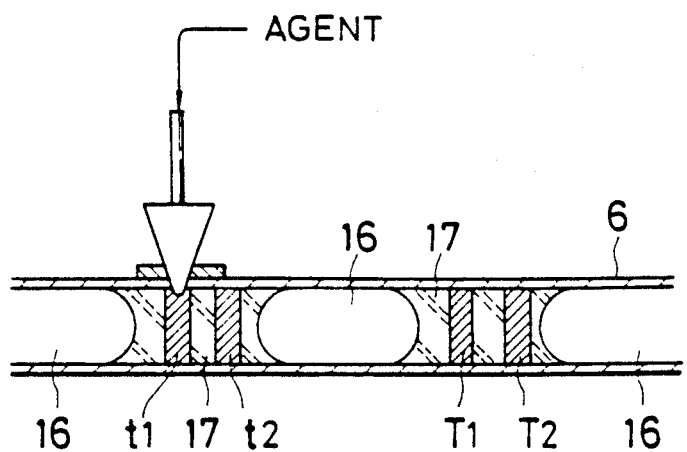
FIG. 6 is an enlarged cross section of the reagent-injecting portion of the bowl shown in FIG. 5.

As described already, the solenoid valves d, e, f, g are connected with the reagent adders 5a, 5b, 5c, 5d, respectively. The valves d, e, f, g are intermittently opened by the sub controllers $cs_2$–$cs_5$, respectively. As an example, the reagent adder 5a introduces glucose oxidase into the conduit 6 via the solenoid valve d that is intermittently opened by the sub controller $cs_2$. As shown in FIG. 6, the reagent is intermittently injected into each aliquot 17 of urine contained in the conduit 6 to form droplets $t_1$, $t_2$, and so on of the reagents inside each aliquot 17.

Since the reagent is intermittently injected into each aliquot 17 of urine in this way, the reagent is well mixed into the urine. Then, the reagent is uniformly dispersed in the urine. As a result, the urine and the reagent are mixed together well.

Then, the aliquots of urine are forced through the conduit 6 and supplied to the concentration-measuring device 8 successively. Thus, the concentration values of different urinary constituents can be successively measured. This series of measurements can be made by the measuring device 8 accurately, because the urine and each reagent are mixed together sufficiently.

Figure 7:
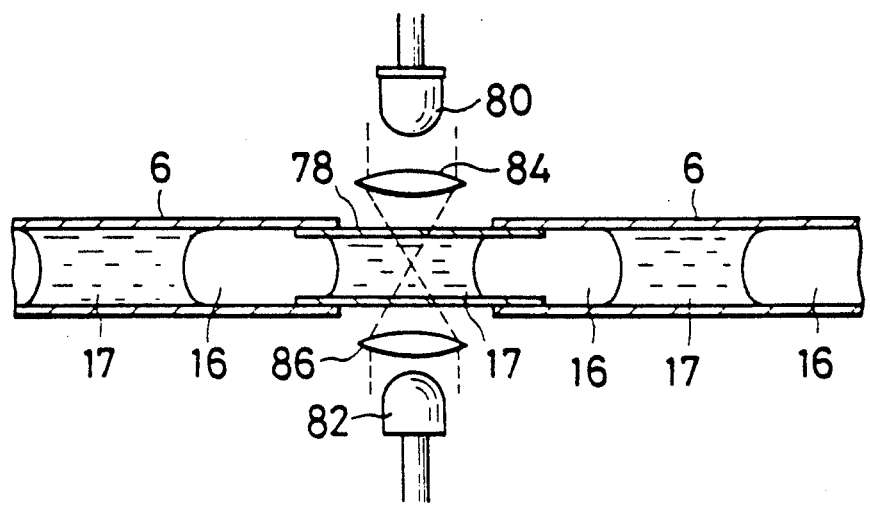
FIG. 7 is a diagram of the light-emitting portion of a further urine constituent-investigating apparatus according to the invention.

Referring next to FIG. 7, there is shown an absorptiometer according to the invention, as well as its surrounding portions. A light-transmitting portion 78 is formed in a conduit 6 and made of a glass tube. A light-emitting diode 80 acting as a light source is disposed opposite to the light-transmitting portion 78. The LED 80 emits light to a sample 17 moving across the light-transmitting portion 78. A photodiode 82 serving as a light-receiving device is disposed opposite to the LED 80. The light transmitted through the sample 17 impinges on the photodiode 82.

Injection of a reagent gives a color to the sample 17. The density of the color varies according to the concentration of a urinary component. A change in the density of the color causes a change in the amount of light falling on the photodiode 82. This is converted into an electrical signal which is then visualized by a display device in the form of numerical values. Consequently, one can immediately know the concentration of the urinary component.

A condenser lens 84 is mounted between the LED 80 and the light-transmitting portion 78. The light emitted by the LED 80 is gathered by the lens 84 and projected into the sample 17 passing through the light-transmitting portion 78.

Another condenser lens 86 is disposed between the light-transmitting portion 78 and the photodiode 82. The light transmitted through the sample 17 is focused onto the photodiode 82 by the lens 86.

In this way, the light produced by the LED 80 is caused to hit the sample 17 efficiently. Also, the light transmitted through the sample 17 is efficiently focused onto the photodiode 82. A change in the concentration of the sample passing through the light-transmitting portion 78 is efficiently transformed into a change in the amount of light received by the photodiode 82. In consequence the concentration of a urinary constituent can be measured with higher accuracy.

It is possible to change the arrangement shown in FIG. 7. For example, the lens located between the light-transmitting portion 78 and the photodiode 82 can be omitted. Conversely, plural kinds of lenses can be disposed between the light-transmitting portion 78 and the LED 80 or between the light-transmitting portion 78 and the photodiode 82.

Instead of directing the light emanating from the light source directly to the sample, the light from the light source may be caused to follow various geometrical paths before impinging into the sample. The light source or the light-receiving device can be a device other than the aforementioned LED and photodiode.

Figure 8:
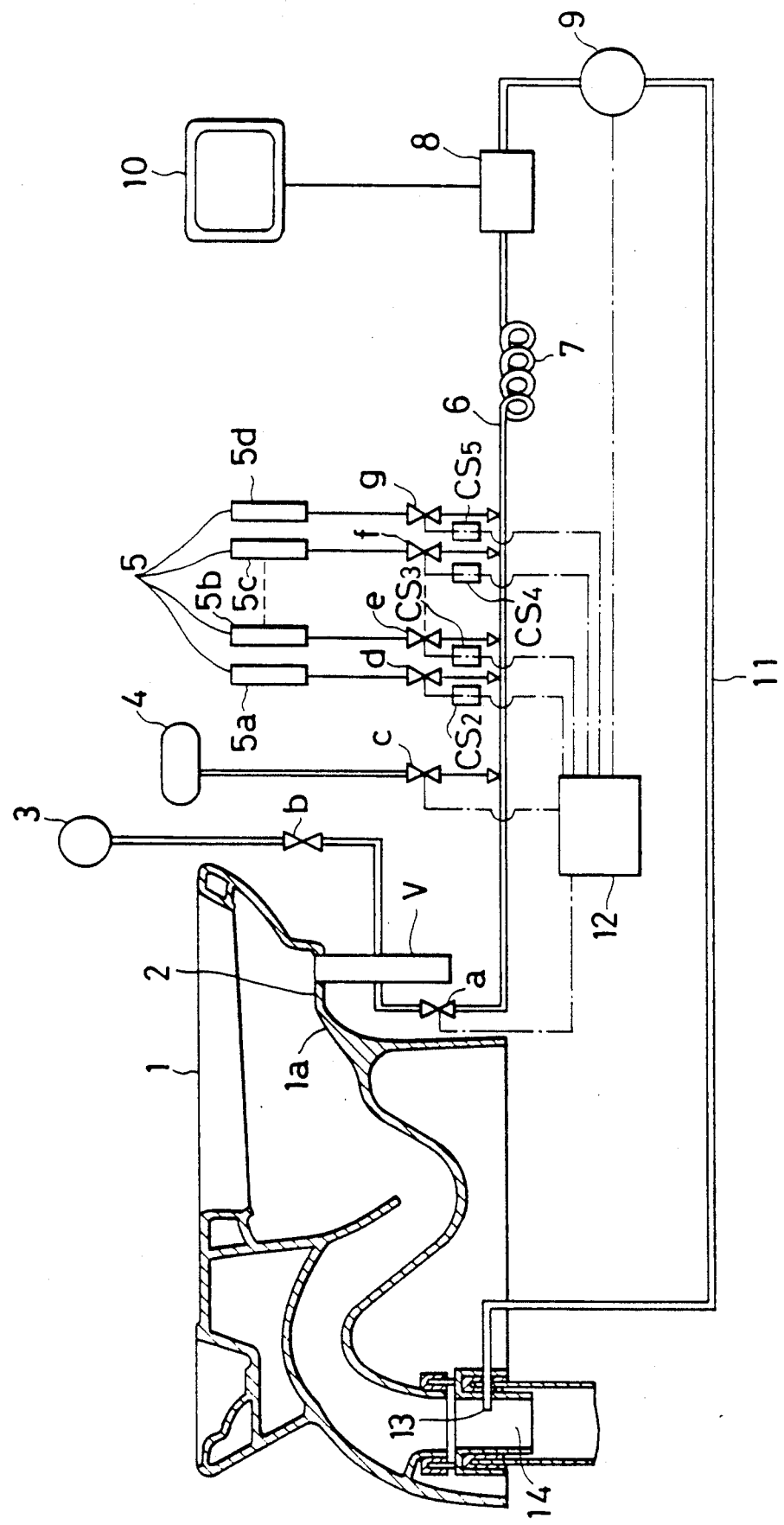
FIG. 8 is a diagram of a still other urine constituent-investigating toilet bowl according to the invention.

Referring to FIG. 8, a further apparatus for investigating urinary constituents in accordance with the invention is schematically shown. The body 1 of the toilet bowl of the apparatus has a lower portion 1a. A substantially horizontally extending horizontal portion 2 is formed ahead of the lower portion 1a. A urine collector V having a top opening depends from the horizontal portion 2. A diluting means 3 for diluting the collected urine by an appropriate factor and a conduit 6 are connected with the collector V. The diluted urine is fed via a conduit 6 to a concentration-measuring device 8 which measures the concentration values of urinary constituents.

A gas injector 4 that intermittently injects gas into the urine present in the conduit 6 is connected to the conduit 6. A group of reagent adders 5 for adding reagents into the urine is also connected to the conduit 6. A mixing coil 7 acting as a mixing means is connected upstream of the concentration-measuring device 8. This apparatus is similar to the apparatus shown in FIG. 5 in other respects.

The urine collected by the urine collector V is mixed with diluting liquid, such as distilled water, supplied from the diluting means 3, inside the collector V to dilute the urine at a given rate of dilution. The flow of the diluted urine from the collector V is controlled by a solenoid valve a and drawn by a suction pump 9. Then, it is introduced into the conduit 6.

The operation of the urine collector V hanging from the horizontal portion 2 of the toilet bowl 1 is now described by referring to the enlarged views of FIGS. 9-12. A urine collection chamber 31 whose opening faces the horizontal portion 2 is formed in the urine collector V. A water chamber 32 separated from the urine collection chamber 31 is formed below the collection chamber 31. A piston 33 extends vertically through the chambers 31 and 32 so as to be movable vertically. The piston 33 has a rod 34 at its lower end. A drive portion (not shown) which is disposed below the rod 34 moves the piston 34 up and down. The piston 33 is mounted so as to be watertight via seal members 35. The piston 33 is capable of compressing the water chamber 32 via a piston ring 36. The inside diameter of the urine collection chamber 31 and the inside diameter of the water chamber 32 are larger than the outside diameter of the piston 33.

Figure 9:
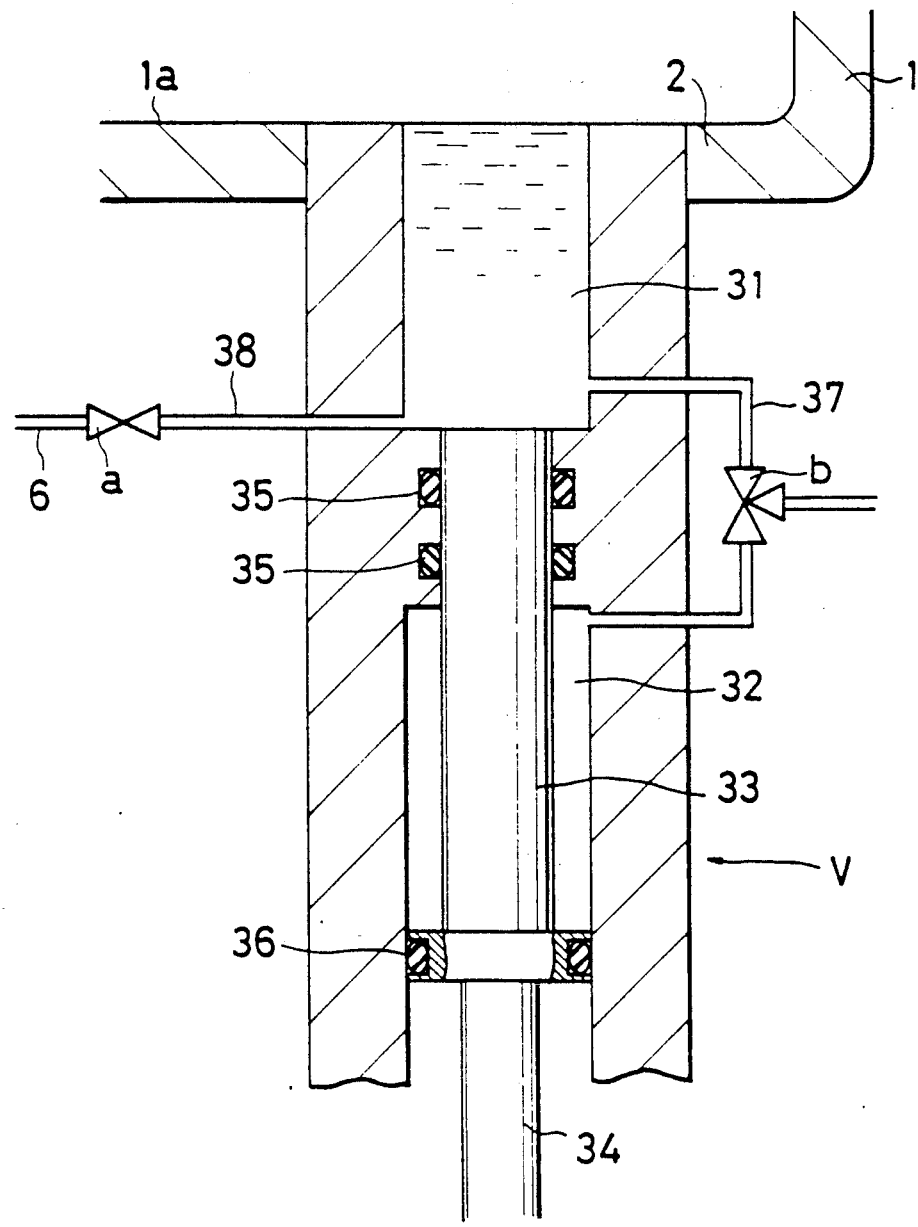
FIGS. 9, 10, 11, and 12 are cross-sectional views of urine-collectors, for illustrating the operation.
Figure 10:
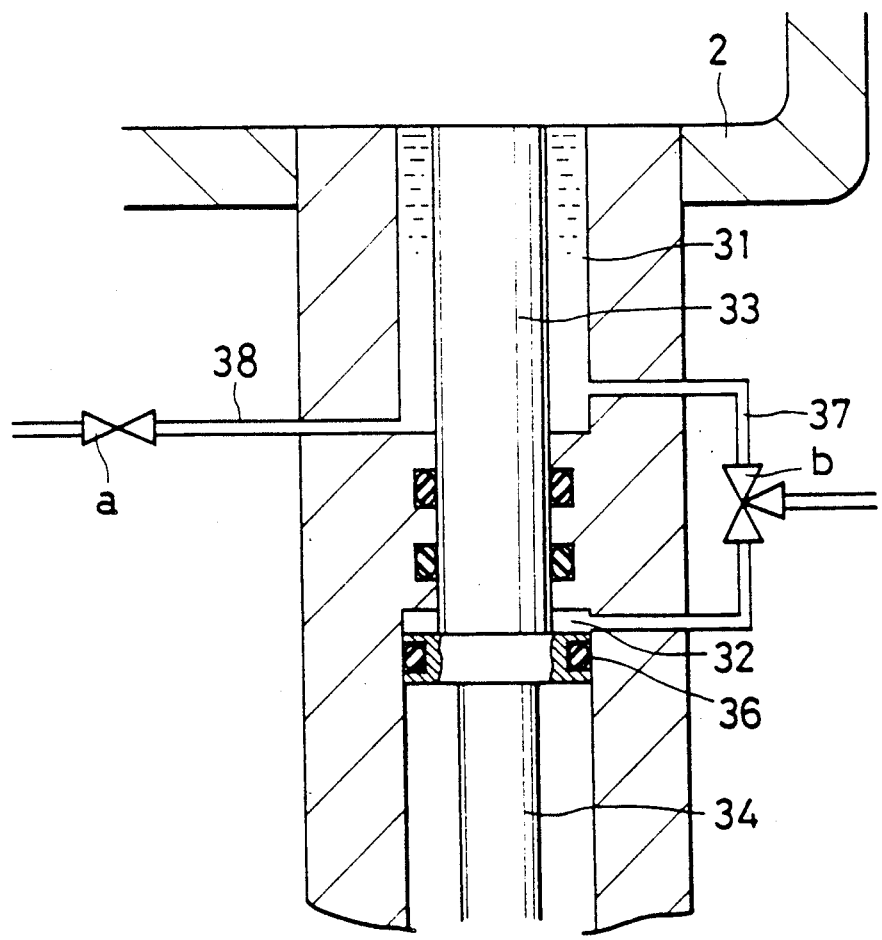
Figure 11:
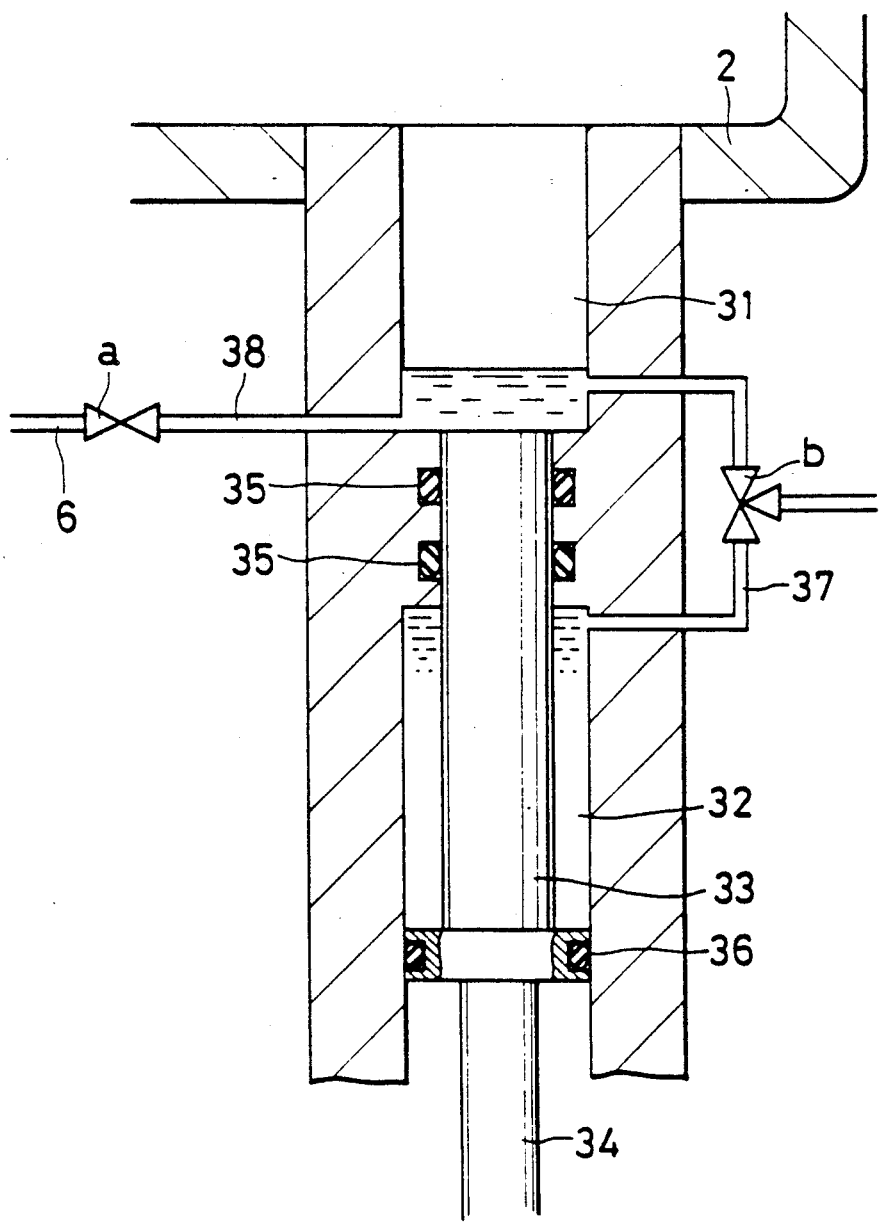

In the condition shown in FIG. 9, the piston 33 is located at its lowermost position. Therefore, urine passed by the user flows into the urine collection chamber 31, thus filling up the chamber 31. In this state, if the piston 33 is raised via the rod 34 as shown in FIG. 10, the urine contained in the collection chamber 31 is pushed outward by the piton 33. A slight amount of urine remains between the outer surface of the piston 33 and the inner surface of the collection chamber 31. Then the piston 33 moves downward as shown in FIG. 11, so that a small amount of urine is taken in the urine collection chamber 31. The downward movement of the piston 33 opens the solenoid vlave b consisting of a three-way solenoid valve. This permits diluting water to be drawn into the water chamber 32 through a connection pipe 37. The diluting water has been previously stored in the diluting means 3.

Figure 12:
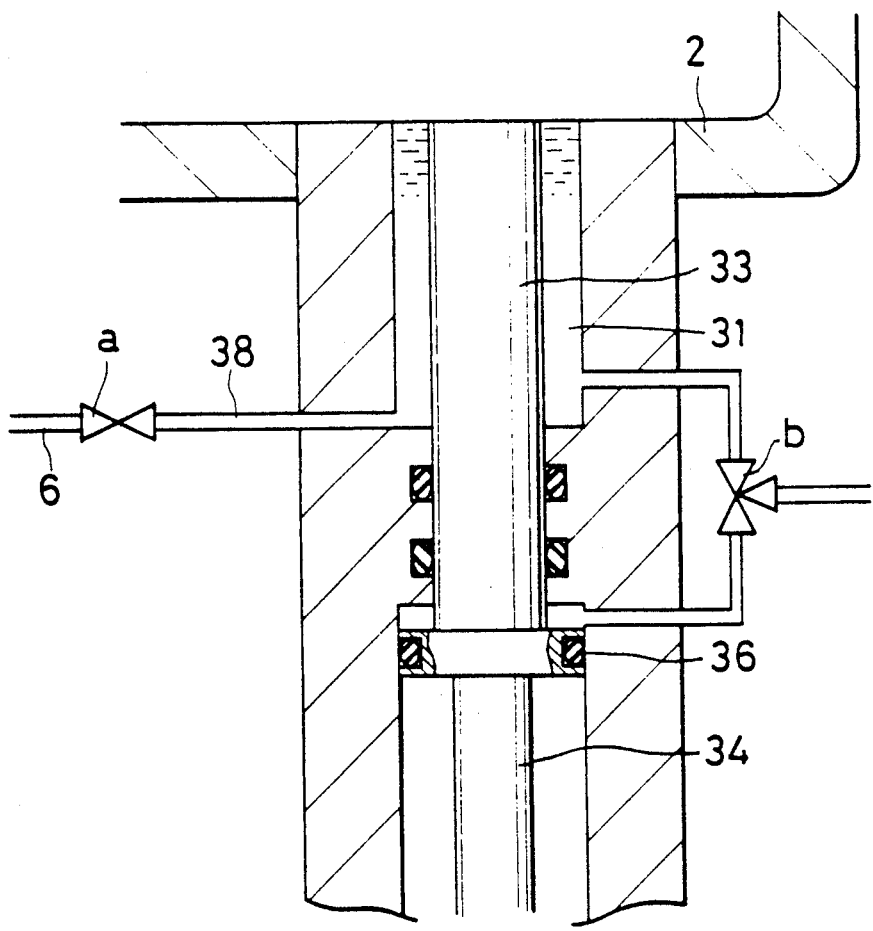

Under this condition, the piston 33 rises again as shown in FIG. 12 to force the water held in the water chamber 32 to the piston ring 36. Then the water is introduced into the dilution chamber 31 via the three-way solenoid valve b. In the chamber 31, the diluting water is mixed with the remaining urine. The excessive urine is again discharged to the outside by the piston 33. Subsequently, the solenoid valve a connected with the urine collection chamber 31 is actuated to force the urine diluted in the collection chamber 31 through a pipe 38 and then through the solenoid valve a, whence the urine enters the conduit 6. The valve a is controlled by the main controller 12. Reagents are added to the urine by reagent adders 5a–5d in the same manner as the apparatus shown in FIG. 5. Thereafter, it is caused to pass through the mixing coil 7 in the conduit 6 to improve the mixing of the urine and the reagents. The aliquots of the urine are then successively admitted into the concentration-measuring device 8. Thus, the concentration values of different urinary components can be successively measured. The urine collector V can also take the form shown in FIGS. 13 and 14.

Figure 13:
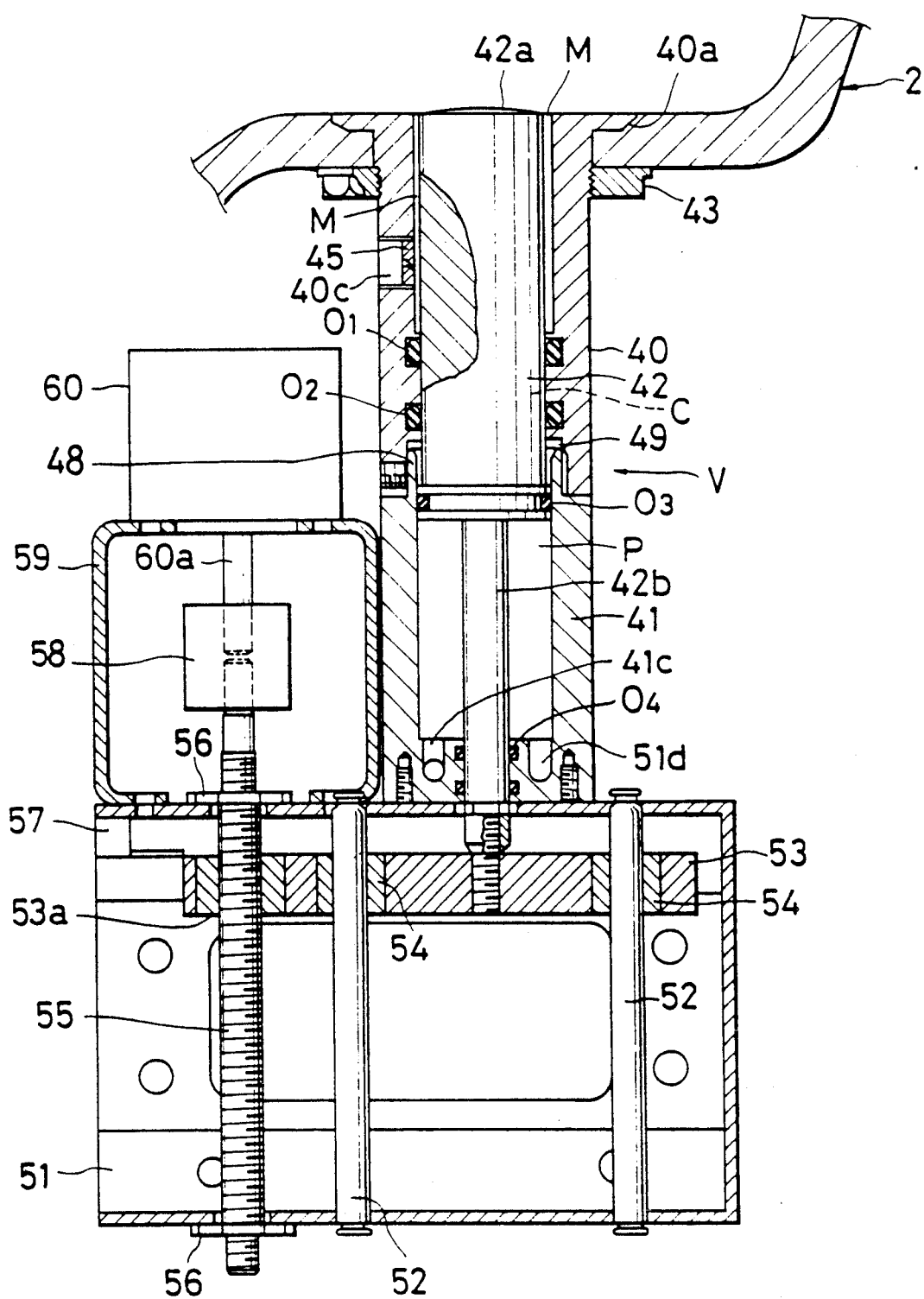
FIG. 13 is a cross-sectional view of other urine collector.

Referring to FIG. 13, the urine collector V comprises a urine-collecting cylinder 40 depending from the horizontal portion 2 of the toilet bowl and a pump cylinder 41 screwed to the lower portion of the collecting cylinder 40 in a coaxial relation with it. A jaw 40a protrudes outwardly from the upper end of the collecting cylinder 40 and is rigidly fixed to the horizontal portion 2. A stationary plate 43 is screwed to the underside of the horizontal portion 2 such that the urine-collecting cylinder 40 is firmly fixed to the horizontal portion 2.

A piston 42 is mounted in the urine-collecting cylinder 40 and in the pump cylinder 41 so as to be movable up and down. 0 rings $0_1$ and $0_2$ are interposed between the inner surface of the collecting cylinder 40 and the piston to secure watertightness. The inside diameter of the upper portion of the collecting cylinder 40 is slightly larger than that of the lower portion to form a slight gap M with the outer surface of the piston 42. Air ports 49 which are in communication with the outside are formed near the junction of the collecting cylinder 40 and the pump cylinder 41. Also, exhaust ports 48 are formed near the junction. The collecting cylinder 40 is provided with an opening 40c at its high position. A nozzle 45 which can spray diluting water into the collecting cylinder 40 is mounted in the opening 40c. Guide holes 41c and 41d communicating with the outside are formed at the bottom of the pump cylinder 41. The inside of the urine-collecting cylinder 40 constitutes a urine collection chamber C. The inside of the pump cylinder 41 forms a pump chamber P.

A piston rod 42b depends from the lower end of the piston 42 and protrudes into a base frame 51 that is connected to the lower end of the pump cylinder 41. The rod 42b is coupled to a slide table 53 disposed inside the base frame 51. The table 53 is able to move vertically inside the frame 51 while guided by a pair of guide bars 52. A nut 53a having an internal thread is formed at the left end of the table 53. A ball thread shaft 55 having a ball thread on its outer surface is threaded onto the nut 53a and rotatably held by ball bearings 56. A stepper motor 60 has a shaft 60a which is connected with the upper end of the shaft 55 via a coupler 58 mounted in a motor frame 59. As the motor 60 is driven, the shaft 55 is rotated in a forward or reverse direction to move the nut 53a upward or downward. This moves the piston rod 42b upward or downward to shift the piton 42 upward or downward in the urine collection chamber C and in the pump chamber P.

Figure 14:
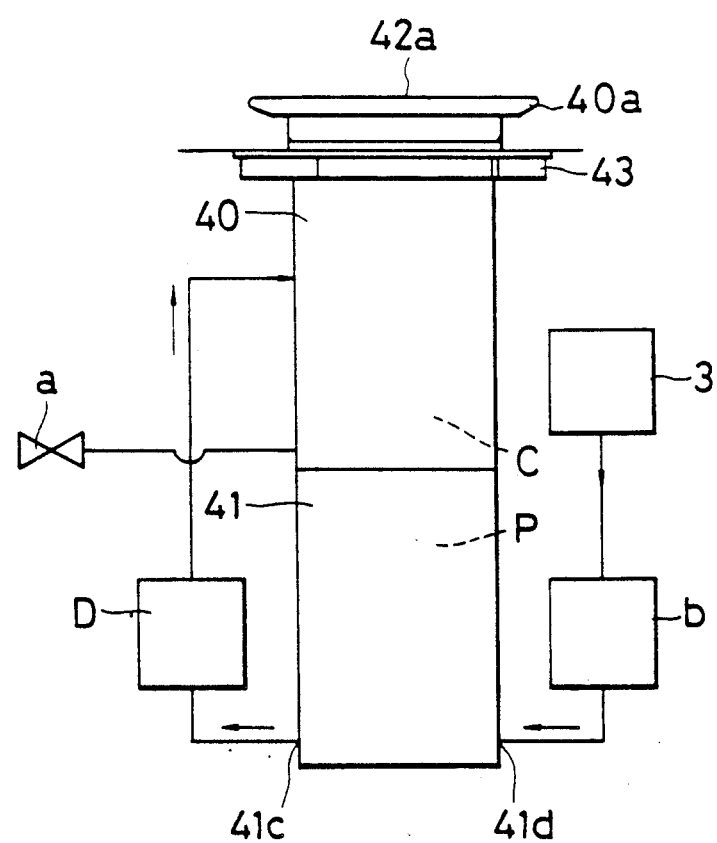
FIG. 14 is a side elevation of the urine collector shown in FIG. 13.

The operation of the urine collector V built as described above in connection with FIG. 13 is next described by referring to FIG. 14. When the piston 42 is located at its lowermost position, the top portion of the urine collecting cylinder 40 is open. Under this condition, a user discharges urine into the cylinder 40. Then, it flows into the urine collection chamber C of the cylinder 40 and is retained there. The stepper motor 60 is driven to move the piston 42 upward. The urine contained in the urine collection chamber C is forced toward the upper end 42a of the piston 42. As a result, most of the urine flows into the lower portion 1a of the bowl along the horizontal portion 2. At this time, a small amount of urine remains in the gap M. When the piston 42 moves upward, a solenoid valve b equipped with a check valve is opened to allow diluting water to be supplied into the pump chamber P from the diluting means 3 via the guide hole 41d. Then, the valve b is closed. Conversely, a solenoid valve D which has a check valve and is located opposite to the valve b is opened. The motor 60 is again reversed to lower the piston 42. The diluting water admitted in the pump chamber P passes through the valve D and reaches the nozzle 35, which then sprays the water into the urine collection chamber C. In this state, the small amount of urine remaining in the urine collection chamber mixes with the diluting water, whereby the urine is diluted well.

Under this condition, the solenoid valve D having the check valve is closed to move the piston 42 upward again, for discharging most of the diluted urine. A small amount of diluted urine is left in the gap M and gathered. Then, the solenoid valve a is opened to draw the gathered thin urine into the conduit 6 by the suction of the pump P, followed by closing of the solenoid valve a. The stepper motor 60 is again driven to move the piston 42 up and down several times. During the upward movement, the diluting water is drawn into the pump chamber P as described previously. During the downward movement, the diluting water held in the pump chamber P is admitted into the urine collection chamber C via the solenoid valve D equipped with the check valve to clean the chamber C well. Thus, preparations are made for the next collection of urine.

The cleaning operation using the vertical reciprocating movement of the piston 42 can be carried out immediately before collection of urine. In this case, the user depresses a control switch or the like to operate the stepper motor 60. This moves the piston 42 up and down as described already and then comes to a stop. Simultaneously, a signal indicating the completion of preparations made for the next collection of urine is produced.

Figure 17:
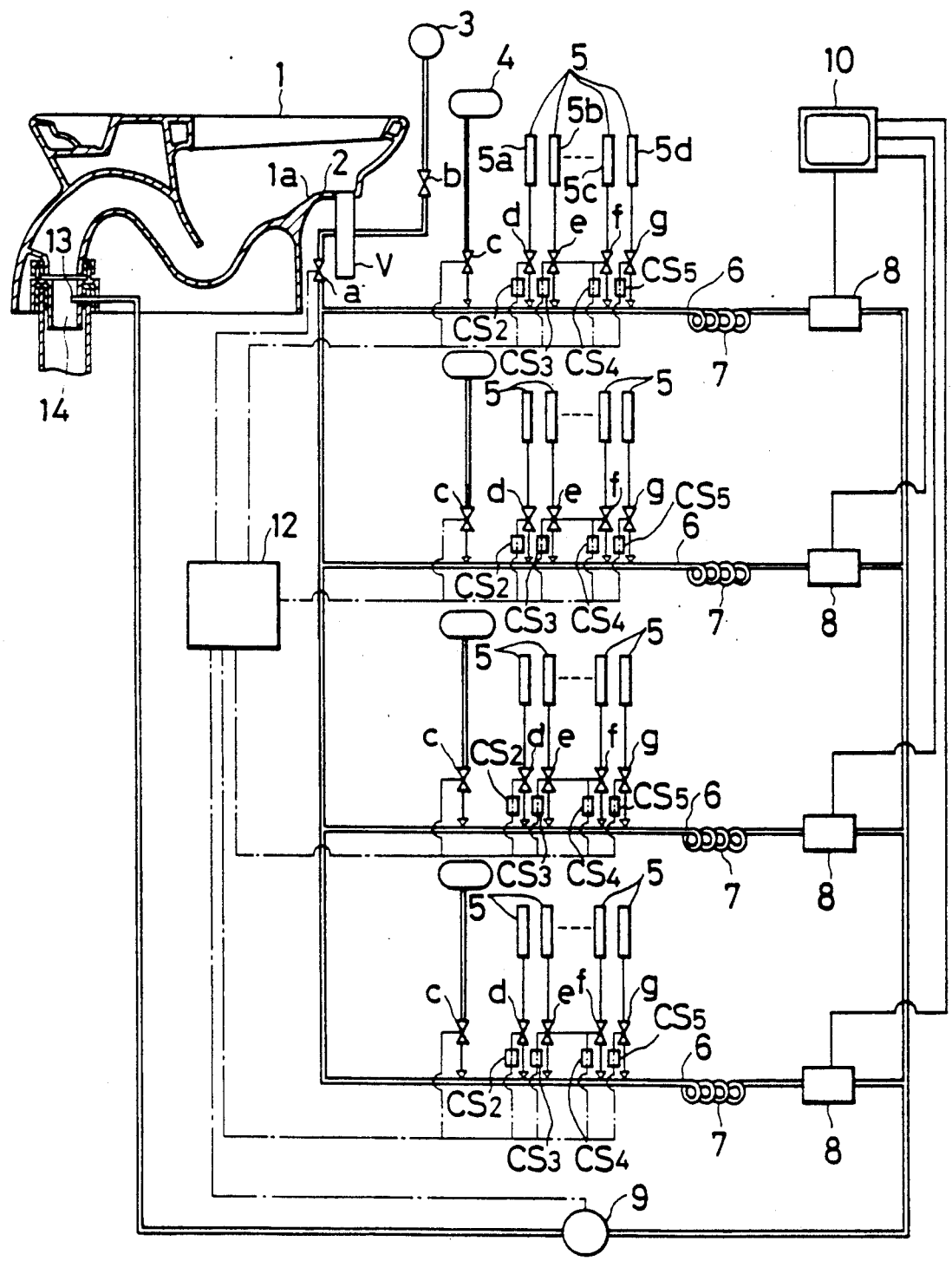
FIG. 17 is a diagram of a yet other measuring apparatus according to the invention.

FIG. 17 shows a yet other apparatus according to the invention. This apparatus has a plurality of conduits 6 each of which is equipped with devices G, C, 5, 5a–5d, c–g, cs₂–cs₅, 7, 8 already described. The output signals from the measuring devices 8 are fed to a common display device 10, where the signals are visualized. The number of the conduits 6 is equal to the number of urinary constituents under investigation. In the illustrated example, the number is four. Since urine is investigated using the conduits simultaneously, the time taken for the measurement is short. This apparatus is not affected by the liquid remaining after reactions.

In the apparatus shown in FIG. 17, the plural conduits 6 are provided. In this case, each conduit 6 can have a pump 9. Further, each two-way valve can be replaced with a three-way valve.

Figure 18:
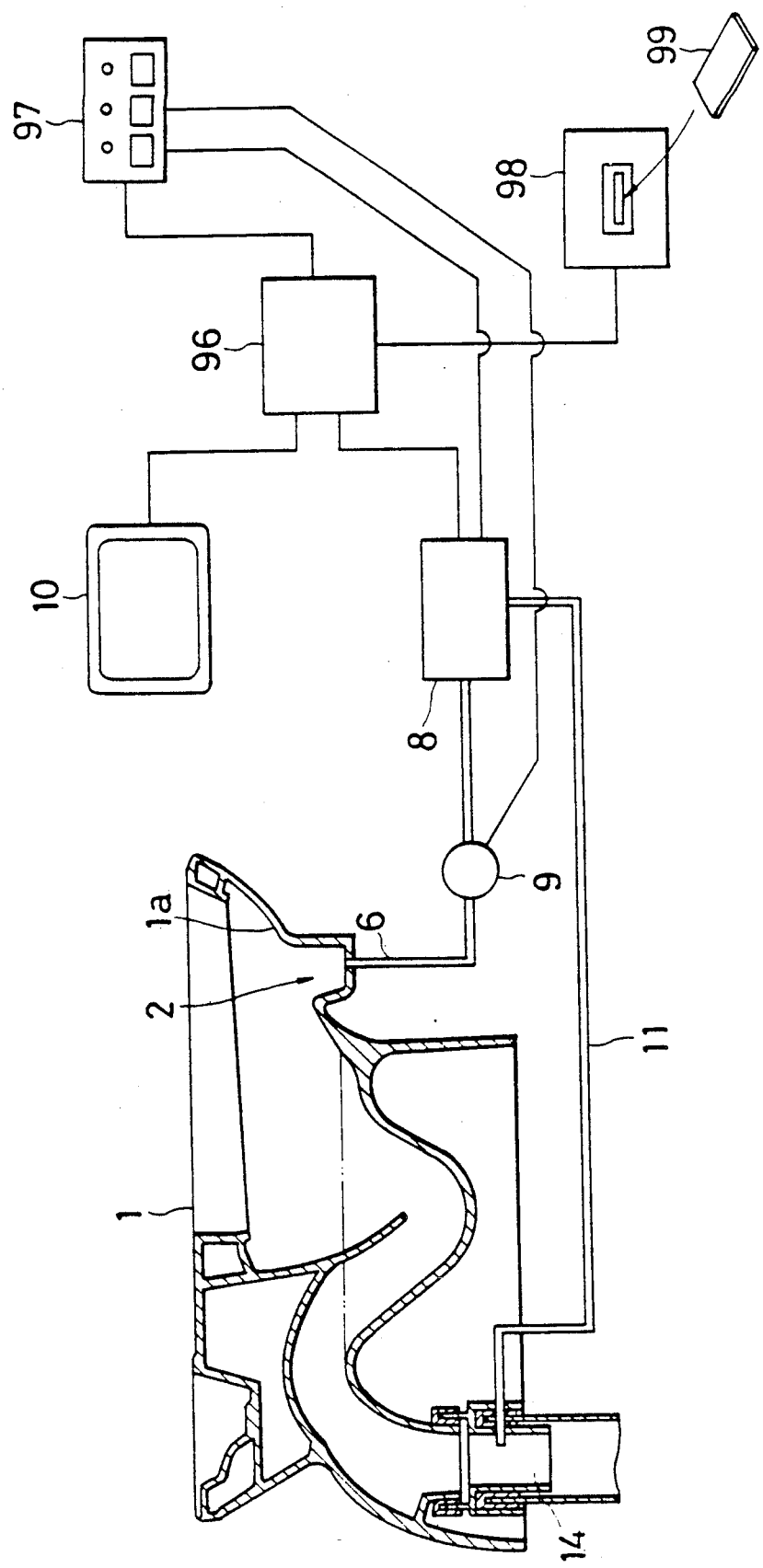
FIG. 18 is a diagram of a still further measuring apparatus according to the invention.

Referring to FIG. 18, there is shown a still further apparatus according to the invention. This apparatus has a toilet bowl 1 including a lower portion 1a. A urine-collecting portion 2 is formed at a suitable position in the lower portion 1a. A conduit 6 is connected with the urine-collecting portion 2. A pump 9 is mounted in the conduit 6 to force the collected urine toward a component analyzer 8. After the urine is analyzed in a given manner, it is discharged via a return passage into a discharge portion 14 formed in the bowl 1.

A signal-processing unit 96 is connected with the component analyzer 8. The unit 96 can act to store the data delivered from the analyzer 8, to read out the stored data, and to appropriately handle data, e.g., it compares the results of the analysis made now with data obtained previously to determine whether the user is in good health or not. A display unit 10 is connected with the processing unit 96 to display the results of processing of data performed by the processing unit 96. An operator's console 97 and data read/write unit 98 are connected with the processing unit 96. The operator manipulates the console 97 to execute an analysis or to display the results of processing of data. The read/write unit 98 stores data about each individual person in his or her IC card 99, i.e., a card on which an integrated circuit is fabricated, and retrieves data about the person from the card 99.

The apparatus shown in FIG. 18 monitors the health of each individual person in the manner described now. The operator operates the console 97 to operate the pump 9, for forcing urine from the urine-collecting portion 2 into the conduit 6. Then, the urine is fed to the component analyzer 8, where the urine is analyzed in a predetermined manner. The analysis can be detection of certain constituents, measurement of concentration, identification of the kinds of constituents, or the like. The output signal from the analyzer 8 which indicates the results of the analysis is supplied to the processing unit 96, where data is processed appropriately. The results of the processing are displayed on the display unit 10 to inform the user of the results. One example of the data processing is to compare the results of the analysis presently made with data previously derived and to calculate the change in the concentration of a constituent. Another example is to compare data obtained now with data obtained when the examinee was in good health, for determining whether the examinee is in good health or not. In this case, data regarding the biorhythm of each individual person, the contents of meal, or other factor can be added as a tool of determining the health to make the judgment more accurate. The results of data processing presented on the display device 5 include numerical values indicating the concentration of a certain constituent, an increase or decrease in the concentration as compared with data obtained previously, graphical representation of changes in the concentration with time, display provided to show whether the examinee is in good health or not, display indicating changes in the health, and display indicating the kind of disease estimated from the concentration values of urinary constituents and from changes in the composition. Of course, the present apparatus can display only the results of analysis made just now or data obtained previously. The display unit 10 can be an aural indicating means, as well as a visual display means.

If a different person uses the toilet bowl, different data previously obtained is needed to handle data. Conveniently, the data read/write device 98 is interfaced to the processing unit 96, and data on each individual person is stored in his or her private IC card 99. In this case, whenever an analysis of urinary components of a person is made, the results of the analysis are stored in the IC card 99. If necessary, data is read from the card and processed. Of course, a memory having the above-described function can be incorporated in the processing unit 96.

While the invention has been particularly shown and described with reference to preferred embodiments thereof, it will be understood by those skilled in the art that the foregoing and other changes in details can be made therein without departing from the spirit and scope of the invention. For example, reagent adders may be disposed beside the conduit going from the urine-collecting portion 2 to the component analyzer 8 to detect certain components, utilizing color reactions. Instead of forming a urine-collecting portion in the lower portion of the toilet bowl, a urinary component detector may be mounted on the surface of the lower portion. Data may be handled according to the output signal from the detector.

What is claimed is:

1. A method of investigating urinary constituents with a measuring device, comprising the steps of:
   collecting urine in a urine collection chamber of a toilet bowl defined by a housing having an open end for receiving the urine, a partition member positioned to divide the housing into said urine collection chamber and a water chamber, said partition member having an opening for receiving a piston, said piston being slidably and sealingly mounted in said opening, said piston having a cross section smaller than the cross section of the urine collection chamber, a lower end of said piston having water tight sealing means in engagement with said water chamber;
   diluting the collected urine by moving said piston into the collection chamber to expel a portion of the collected urine, withdrawing the piston from the collection chamber, and adding diluting liquid from said water chamber to the remaining portion of the collected urine, said water chamber having inlet and outlet means for receiving and discharging water, conduit means for delivering and discharging water from said water chamber, means in said conduit means for controlling the flow of water to the inlet and outlet means of said water chamber, said conduit means being operatively connected to an inlet in said urine collection chamber, said urine collection chamber having an outlet means for delivering the urine sample;
   forcing the diluted urine into a conduit to supply the urine to the measuring device;
   injecting gas into the urine contained in the conduit to divide the urine into plural aliquots which are separated from each other by intervening gas; and
   introducing the aliquots successively into the measuring device to investigate constituents of the aliquots.

2. A method of investigating urinary constituents as set forth in claim 1, wherein the step of injecting gas into the urine involves intermittently injecting the gas to divide the urine contained in the conduit into the aliquots.

3. A method of investigating urinary constituents as set forth in claim 1, further including the step of diluting each aliquot at a desired rate of dilution after the urine contained in the conduit is divided into the aliquots by intermittently injecting gas into the conduit.

4. A method of investigating urinary constituents as set forth in claim 1, wherein a different reagent is added to each different aliquot of the urine which is separated in the conduit.

5. A method of investigating urinary constituents as set forth in claim 1, wherein reagents of the same kind but having different values of concentration are added to the aliquots of the urine which are separated in the conduit.

6. A method of investigating urinary constituents as set forth in claim 1, further including the steps of mixing together the urine and the reagents to form homogeneous mixtures after the reagents are added to the aliquots of urine which are separated in the conduit.

7. An apparatus for investigating urinary constituents, comprising:
   a toilet bowl having a urine-collecting portion, said urine-collecting portion comprised of a water chamber having inlet and outlet means for receiving and discharging water and a urine collection and dilution chamber defined by a housing having an open end for receiving the urine, a partition member positioned to divide the housing into said urine collection and dilution chamber and said water chamber, said partition member having an opening for receiving a piston, said piston being slidably and sealingly mounted in said opening, said piston having a cross section smaller than the cross section of the urine collection and dilution chamber, a lower end of said piston having water tight sealing means in engagement with said water chamber, wherein said water chamber further comprises conduit means for delivering and discharging water from said water chamber, means in said conduit means for controlling the flow of water to the inlet and outlet means of said water chamber, said conduit means being operatively connected to an inlet in said urine collection and dilution chamber, said urine collection and dilution chamber having an outlet means for delivering the urine sample;
   a measuring device for detecting constituents of urine;
   a conduit for forcing urine from the urine-collecting portion into the measuring device; and
   an injection means for injecting gas into the conduit such that the injected gas divides the urine contained in the conduit into aliquots.

8. An apparatus for investigating urinary constituents as set forth in claim 7, wherein a means for diluting urine is mounted either in the urine-collecting portion of the toilet bowl or beside the conduit.

9. An apparatus for investigating urinary constituents as set forth in claim 7, wherein a reagent adder is disposed beside the conduit and downstream of the injection means.

10. An apparatus for investigating urinary constituents as set forth in claim 8, wherein a reagent adder is mounted beside the conduit and downstream of both the injection means and the diluting means.

11. An apparatus for investigating urinary constituents as set forth in claim 9, wherein a means for mixing together urine and the reagent is mounted beside the conduit and between the reagent adder and the measuring device that measures concentration of a urinary constituent.

12. An apparatus for investigating urinary constituents as set forth in claim 11, wherein the mixing means consists of a spirally shaped tube.

13. An apparatus for investigating urinary constituents as set forth in claim 7, wherein the measuring device is a spectrophotometer which measures concentration.

14. An apparatus for investigating urinary constituents as set forth in claim 7, wherein a display device that displays the results of a measurement is connected with the measuring device for measuring concentration.

15. An apparatus for investigating urinary constituents as set forth in claim 1, further including the step of intermittently injecting a reagent into each aliquot of urine with a reagent adder to measure the concentration of a constituent of each aliquot.

16. An apparatus for investigating urinary constituents as set forth in claim 7, further including a reagent adder disposed beside the conduit and downstream of the injection means, the reagent adder being capable of intermittently injecting a reagent into each aliquot of urine separated by the gas.

17. An apparatus for investigating urinary constituents as set forth in claim 7, wherein said measuring device includes a light-transmitting portion through which urine flows, a light source, a light-receiving device disposed on the opposite side of the light-transmitting portion from the light source, and a lens mounted between the light source and the light-transmitting portion for focusing light into the urine, the light-transmitting portion being made from a material that transmits light.

18. An apparatus for investigating urinary constituents as set forth in claim 7, further including
a reagent adder mounted beside the conduit and capable of injecting a reagent into the conduit.

19. An apparatus for investigating urinary constituents as set forth in claim 17, wherein said light source consists of two or more light-emitting means emitting different wavelengths of light.

20. An apparatus for investigating urinary constituents as set forth in claim 7, wherein a plurality of conduits are provided, and wherein each conduit is equipped with the injection means and the measuring device.

21. An apparatus for measuring urinary constituents, comprising:

a toilet bowl having a urine-collecting portion, said urine-collecting portion comprised of a water chamber having inlet and outlet means for receiving and discharging water and a urine collection and dilution chamber defined by a housing having an open end for receiving the urine, a partition member positioned to divide the housing into said urine collection and dilution chamber and said water chamber, said partition member having an opening for receiving a piston, said piston being slidably and sealingly mounted in said opening, said piston having a cross section smaller than the cross section of the urine collection and dilution chamber, a lower end of said piston having water tight sealing means in engagement with said water chamber, wherein said water chamber further comprises conduit means for delivering and discharging water from said water chamber, means in said conduit means for controlling the flow of water to the inlet and outlet means of said water chamber, said conduit means being operatively connected to an inlet in said urine collection and dilution chamber, said urine collection and dilution chamber having an outlet means for delivering the urine sample;

a constituent analyzer for analyzing the urinary constituents;

a conduit for forcing the urine collected in the urine-collecting portion into the constituent analyzer;

a processing unit for storing output data from the analyzer, reading stored data and processing data in a desired manner; and a display means for displaying the results of data processing delivered from the processing unit.

22. An apparatus for measuring urinary constituents, comprising:

a toilet bowl having a lower portion in which a device for investigating urinary constituents is mounted, the device including a water chamber having inlet and outlet means for receiving and discharging water and a urine collection and dilution chamber defined by a housing having an open end for receiving the urine, a partition member positioned to divide the housing into said urine collection and dilution chamber and said water chamber, said partition member having an opening for receiving a piston, said piston being slidably and sealingly mounted in said opening, said piston having a cross section smaller than the cross section of the urine collection and dilution chamber, a lower end of said piston having water tight sealing means in engagement with said water chamber, wherein said water chamber further comprises conduit means for delivering and discharging water from said water chamber, means in said conduit means for controlling the flow of water to the inlet and outlet means of said water chamber, said conduit means being operatively connected to an inlet in said urine collection and dilution chamber, said urine collection and dilution chamber having an outlet means for delivering the urine sample;

a processing unit for storing output data from the device, reading stored data and processing data in a desired manner; and a display means for displaying the results of data processing delivered from the processing unit.

* * * * *